United States Patent

Modrcin et al.

[11] Patent Number: 6,071,858
[45] Date of Patent: Jun. 6, 2000

[54] STABLE, DRY COMPOSITIONS FOR USE AS HERBICIDES

[75] Inventors: Thomas F. Modrcin, Liberty, Mo.; Vijay C. Desai, Shawnee, Kans.; Peter E. Newallis, Leawood, Kans.; Klaus Jelich, Overland Park, Kans.; John W. Brandriff, Blue Springs, Mo.; Dennis E. Jackman, Prairie Village, Kans.

[73] Assignee: Bayer Corporation, Pittsburgh, Pa.

[21] Appl. No.: 09/165,139

[22] Filed: Oct. 1, 1998

Related U.S. Application Data

[63] Continuation-in-part of application No. 08/989,488, Dec. 12, 1997, abandoned.

[51] Int. Cl.[7] .................................................. A01N 43/64
[52] U.S. Cl. .............................................................. 504/134
[58] Field of Search ............................................. 504/134

[56] References Cited

U.S. PATENT DOCUMENTS

| | | | |
|---|---|---|---|
| 4,614,799 | 9/1986 | Tocker | 544/182 |
| 5,593,942 | 1/1997 | Santel et al. | 504/134 |
| 5,759,955 | 6/1998 | Santel et al. | 504/132 |
| 5,792,872 | 8/1998 | Prasad et al. | 548/136 |
| 5,863,865 | 1/1999 | Lee et al. | 504/271 |

FOREIGN PATENT DOCUMENTS

| | | |
|---|---|---|
| 0 494 386 | 7/1992 | European Pat. Off. . |
| 97/27748 | 8/1997 | WIPO . |
| 97/34486 | 9/1997 | WIPO . |

*Primary Examiner*—Jose' G. Dees
*Assistant Examiner*—Alton Pryor
*Attorney, Agent, or Firm*—Joseph C. Gil; Carol Marmo

[57] ABSTRACT

The present invention relates to a dry composition that can be used as a herbicide. The composition contains N-(4-fluorophenyl)-N-(1-methylethyl)-2-[[5-(trifluoromethyl)-1,3,4-thiadiazol-2-yl]oxy]acetamide, 4-amino-6-(1,1-dimethylethyl)-3-(methylthio)-1,2,4-triazin-5-(4H)-one, and a pH adjusting agent. The pH adjusting agent is present in an amount such that it constitutes from about 0.1% to about 10% of the composition, and the resulting pH is from about 2.8 to about 5.4. The molar ratio of 4-amino-6-(1,1-dimethylethyl)-3-(methylthio)-1,2,4-triazin-5-(4H)-one to N-(4-fluorophenyl)-N-(1-methylethyl)-2-[[5-(trifluoromethyl)-1,3,4-thiadiazol-2-yl]oxy]acetamide in the composition is from about 1:1 to about 1:6.

14 Claims, 1 Drawing Sheet

STABLE, DRY COMPOSITIONS FOR USE AS HERBICIDES

This application is a Continuation-In-Part of application Ser. No. 08/989,488, filed Dec. 12, 1997 now abandoned.

TECHNICAL FIELD OF THE INVENTION

The present invention relates to a stable dry herbicidal composition that contains N-(4-fluorophenyl)-N-(1-methylethyl)-2-[[5-(trifluoromethyl)-1,3,4-thiadiazol-2-yl]oxy]acetamide, 4-amino-6-(1,1-dimethylethyl)-3-(methylthio)-1,2,4-triazin-5-(4H)-one, and a pH adjusting agent. The pH adjusting agent is present in an amount such that it constitutes from about 0.1% to about 10.0% by weight of the composition, and the resulting pH of the composition is from about 2.8 to about 5.4. In a preferred embodiment, the pH adjusting agent is citric acid.

BACKGROUND OF THE INVENTION

Agricultural formulations can be constructed to contain more than one active ingredient (a.i.) in a formulation. Examples of commercial herbicides that contain two active ingredients in a single formulation include alachlor/atrazine, bromacil/diuron, alachlor/ glyphosate, clomazone/ trifluralin, cyanazine/atrazine, and 2,4-D/2,4-MCPA. Combining active ingredients is advantageous because it allows the formulated product to be efficacious over a broader range of target pests. However, combining multiple active ingredient materials in a single formulation can be problematical, and may not always be attainable. Pairing active ingredients is highly ingredient specific, and it must first be established that the actives are chemically stable in the presence of one another. It is not uncommon that when two complex organic molecules, such as pesticide active ingredients, are brought together that a chemical incompatibility exists that causes one or both of the active ingredients to undergo a change in its chemical identity. These changes can be due to chemical interactions occurring at reactive sites on either or both of the compounds involved, or reactions catalyzed by reactive impurities that may be present. The rate of these reactions, and therefore the extent of the chemical change observed, may be rapid or slow. In practice, the progress of the reaction, or lack thereof, in a formulated pesticide can be followed by conducting chemical assays of the product over a period of time, and recording the percent loss of active ingredient. Since chemical reactions are temperature dependent, one may even conduct assays at various storage temperatures and, with the aid of classical reaction-kinetics techniques, determine the rate constant of the reaction and the half-life of the actives. Such calculations are often used to estimate the shelf-life of a product.

When a chemical instability is discovered between two actives, various remedies to the problem may be considered. These generally fall into two categories namely, chemical modification and physical separation. Chemical modification approaches include: (i) selecting actives that are more chemically similar and therefore less likely to be antagonistic; (ii) conducting site-specific reactions during the manufacturing process to block or alter the offending site; or, if the loss in active ingredient is minor, (iii) adding compensatory active to the formulation during its manufacture. The physical separation options include any treatment that keeps the actives physically separated while still ostensibly presenting a single formulated system. These options include (i) microencapsulation; (ii) inclusion complexation; (iii) application of external water-soluble film coatings such as polyvinylpyrrolidone; (iv) employing compartmentalized packaging including water-soluble pouches; or, in the case of water dispersible granules, (v) employing a simple physical mix of each active granulated separately.

However, many of these approaches are undesirable as they usually entail extensive addition research, increased costs and other disadvantages. For example, altering the chemical structure of the active ingredient in order to neutralize a reactive site may change its biological effectiveness. Microencapsulation and complex formation are research intensive procedures with high raw material and processing costs. Physical mixes of two separately granulated dry flowables are subject to classification and segregation in the package if the granular size and density is not perfectly matched.

N-(4-fluorophenyl)-N-(1-methylethyl)-2[[5-(trifluoromethyl)-1,3,4-thiadiazol-2-yl]oxy]acetamide, also known as "Fluthiamide" or "Flufenacet," and 4-amino-6-(1,1-dimethylethyl)-3-(methylthio)-1,2,4-triazin-5-(4H)-one, also known as "Metribuzin," are two selective herbicides, from two distinctly different chemical families, which are highly effective against a range of broadleaf and grassy weeds found in corn and soybeans. Either of these active ingredients, when used by itself in a formulation, is stable during storage. However, when combined in a single formulation, as in the preferred dry form, these active ingredients are susceptible to chemical degradation. Therefore, there is a need to provide a dry agricultural composition, preferably a water-dispersible granule, of Fluthiamide and Metribuzin that is chemically stable and has commercially acceptable handling and biological performance properties.

BRIEF SUMMARY OF THE INVENTION

The present invention relates to a stable dry flowable, wettable powder, or other dry composition containing N-(4-fluorophenyl)-N-(1-methylethyl)-2-[[5-(trifluoromethyl)-1,3,4-thiadiazol-2-yl]oxy]acetamide, 4-amino-6-(1,1-dimethylethyl)-3-(methylthio)-1,2,4-triazin-5-(4H)-one, and a pH adjusting agent. The pH adjusting agent is present in an amount such that it constitutes from about 0.1% to about 10% by weight of the composition, and the resulting pH of the composition is from about 2.8 to about 5.4. In a preferred embodiment, the pH adjusting agent is citric acid.

Generally, there are several ways to adjust the pH of a composition. In the process of the present invention, the 4-amino-6-(1,1-dimethylethyl)-3-(methylthio)-1,2,4-triazin-5-(4H)-one ("Metribuzin") may be treated with an inorganic or organic acid prior to its use in the composition. Suitable organic or inorganic acids include sulfuric acid, nitric acid, hydrochloric acid, phosphoric acid, a carboxylic acid, a dicarboxylic acid and mixtures thereof.

However, if the Metribuzin is not treated with an acid prior to adding N-(4-fluorophenyl)-N-(1-methylethyl)-2[[5-(trifluoromethyl)-1,3,4-thiadiazol-2-yl]oxy]acetamide ("Fluthiamide" or "Flufenacet"), the pH adjusting agent is then added to the mixture of Metribuzin and Fluthiamide. Suitable pH adjusting agents include citric acid, ammonium and potassium salts of sulfuric and phosphoric acids that are acidic in nature, and mixtures thereof.

Further, the composition of the present invention may be converted into a suitable formulation type, preferably a dry flowable.

DETAILED DESCRIPTION OF THE INVENTION

Figure 1:
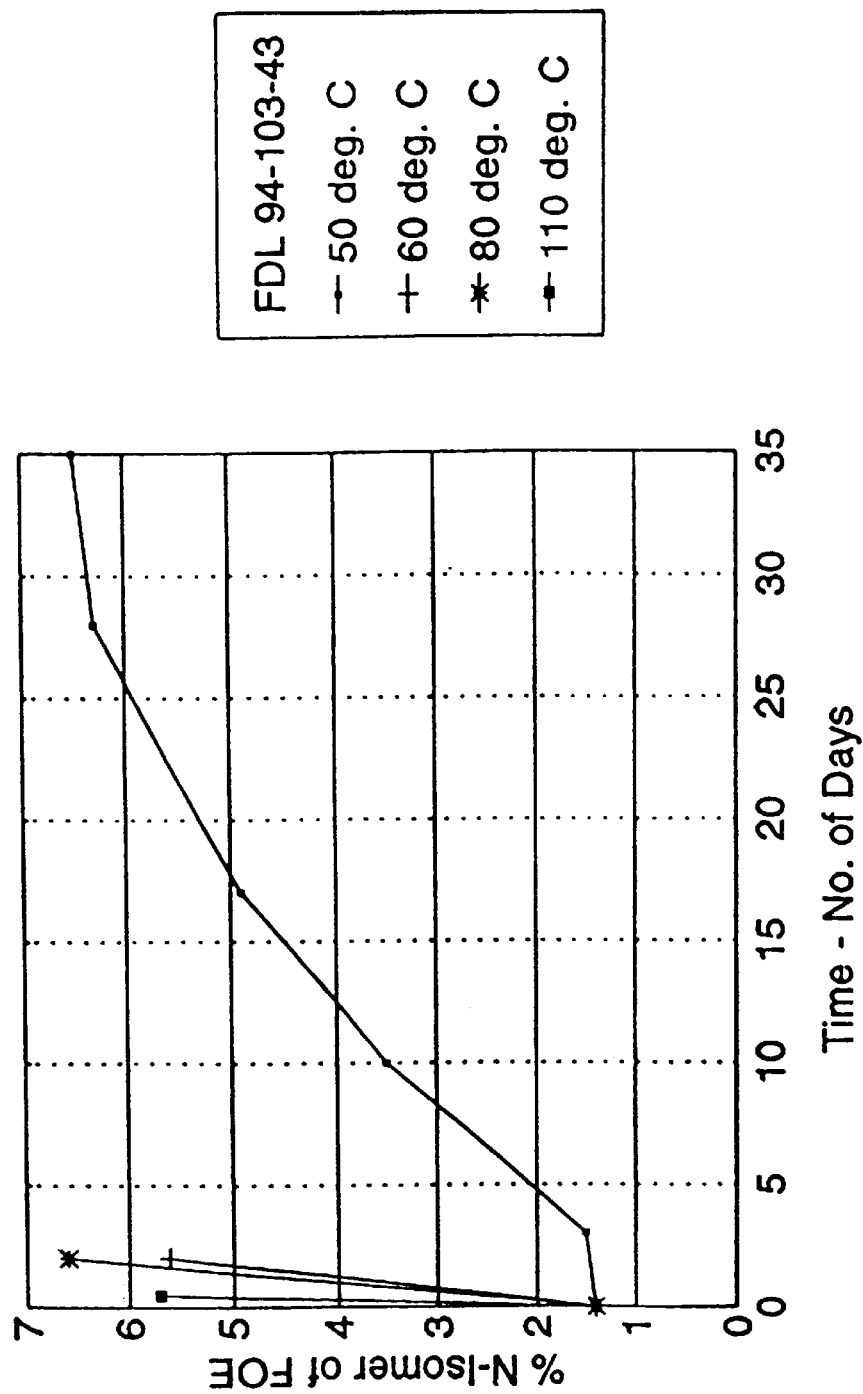
FIG. 1: Depicts Accelerated Stability Test Results to Real-Time Storage.

The present invention relates to a stable dry flowable, wettable powder, or other dry composition that contains the active ingredients N-(4-fluorophenyl)-N-(4-methylethyl)-2-[[5-(trifluoromethyl)-1,3,4-thiadiazol-2-yl]oxy]acetamide, hereinafter referred to as "Fluthiamide," and 4-amino-6-(1,1-dimethylethyl)-3-(methylthio)-1,2,4-triazin-5-(4H)-one, hereinafter referred to as "Metribuzin". A pH adjusting agent is added to the mixture of Fluthiamide and Metribuzin. With the addition of a pH adjusting agent, the composition exhibits improved stability against the hydrolysis and N-isomerization of the active ingredients.

A dry composition containing the active ingredients Fluthiamide and Metribuzin, and a pH adjusting agent, can be prepared in several ways. In one embodiment, the Fluthiamide and Metribuzin are combined in a mixing vessel such as a ribbon blender or high intensity plow mixer. A pH adjusting agent is added to the vessel containing the active ingredient mixture. Suitable pH adjusting agents for use in the present invention include citric acid, ammonium and potassium salts of sulfuric acid and phosphoric acid, and mixtures thereof. A preferred pH adjusting agent is citric acid.

The amount of pH adjusting agent present in the composition is such that it constitutes from about 0.1% to about 10% by weight of the composition. The resulting pH of the composition is from about 2.8 to about 5.4.

In another embodiment, the pH of the composition is adjusted by acidifying the Metribuzin prior to its addition to the composition. In this acidification step, the Metribuzin can be treated with an inorganic or organic acid. Suitable inorganic acids include sulfuric acid, nitric acid, hydrochloric acid and phosphoric acid. Suitable organic acids include carboxylic acids and dicarboxylic acids. Examples of carboxylic acids that can be used are aliphatic acids such as acetic and formic acid, or aromatic acids such as benzoic or salicylic acid. Examples of dicarboxylic acids that can be used are oxalic, phthalic, sebacic and adipic acids.

The procedure for acidifying the Metribuzin can include washing the Metribuzin in a funnel with an inorganic acid such as phosphoric acid. Following washing with the inorganic or organic acid, the Metribuzin may be rinsed with distilled water. If the Metribuzin is rinsed with distilled water after being treated with the acid, it is preferably dried, such as under a vacuum, prior to its use in the composition.

Following acidification, the Metribuzin is combined with the Fluthiamide in a mixing vessel such as a ribbon blender or high intensity plow mixer. The addition of a pH adjusting agent further adjusts the pH of the composition. However, the amount of the pH adjusting agent added to the composition may be less than the amount added to the composition when the Metribuzin is not acidified prior to its addition to the composition. The pH-adjusted mixture is then converted into a commercial grade dry herbicide composition such as a water dispersible powder, or wettable powder (WP), or more preferably to a water dispersible granule (WDG or "Dry Flowable"), by various dry processing techniques known in the art.

The molar ratio of Fluthiamide to Metribuzin is from about 1:1 to about 6:1. It is preferable that the Fluthiamide used in the reaction mixture is present in a molar excess compared to the Metribuzin. Preferably, the molar ratio of Fluthiamide to Metribuzin is from about 1.2:1 to about 2.5:1.

Although the preferred embodiment is a wettable powder or dry flowable mixture, the composition of the present invention can be converted to other customary formulations, such as emulsions, suspensions, dusting agents, pastes, suspension-emulsion concentrates, carrier granules impregnated with active compound, capsules in polymeric casings, micro encapsulations, dry compacts, and tablets.

These formulations are produced using any appropriate technique known in the art. For example, the active compounds may be mixed with standard formulation aids, commonly used in agricultural formulations, such as, extenders, liquid solvents, solid carriers or inert fillers, surface-active agents such as, emulsifying agents, wetting agents, dispersing agents, defoamers and the like. When water is used as an extender in emulsions, organic solvents can also be used as auxiliary solvents. Liquid solvents that can be used include aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulfoxide, as well as water.

The preferred dry compositions of the invention may be prepared by any of the customary techniques for processing either wettable powders or water-dispersible granules known in the art. To prepare a wettable powder, the pH-adjusted admixture is blended with suitable formulation aids and milled to a requisite particle size suitable for sustained self-suspensibility in water. To prepare a water-dispersible granule or dry flowable material, the pH-adjusted composition is similarly admixed with formulation aids for proper disintegration and suspension properties. The admixture is then milled and granulated by any of a variety of granulation processes, including pan granulation, extrusion, or Schugi processing for example. The pH-adjusted admixtures would also lend themselves to other processes for producing dry compositions, such as spray drying, spray agglomeration, and dry compaction.

Examples of the types of solid carriers or inert fillers that can used in the invention include ground natural minerals or clays, such as kaolin, talc, chalk, quartz, attapulgite, dolomite, montmorillonite, diatomaceous earth, and the like;

or ground or air-floated synthetic minerals, such as highly-dispersed silica, fumed silica, alumina, and silicates. Solid inerts that can be used as granular carriers include crushed and fractionated natural minerals such as calcite, marble, pumice, sepiolite, attapulgite, dolomite, and montmorillonite, as well as processed organic materials such as meals, sawdust, coconut shells, peanut hulls, corn cobs, tobacco stalks, and the like including synthetic materials and reprocessed industrial byproducts.

Suitable surface active agents, or mixtures thereof, that can be used include nonionic and anionic emulsifiers, wetting agents, and dispersants; such as polyethylene-fatty acid esters, phosphate esters, ethoxylated alkyl phenols, polyoxyethylene-fatty alcohol ethers, alkylaryl polyglycol ethers, sodium mono- and di-alkyl-sulfonates, sodium alkylsulfate, sodium mono- and di-alkylarylsulfonates, sulfonated kraft lignins, hydroxyalkylmethylcelluloses, polyoxyalkylene block copolymers, sodium alpha-olefin sulfonate, alkylnaphthalene sulfonate formaldehyde condensate, alkyl diphenylether sulfonates, alkyl diphenyloxide disulfonates, polycarboxylates, organosilicone block copolymers, derivatives of the N-methyl fatty acid taurides, sulfo-succinates, tristyrylphenols, ethoxylated alkylamines, alkylpolyglucosides, salts of dodecylbenzene sulfonic acid, and the like, including sodium, potassium, ammonium and amine salts.

The following examples are presented to demonstrate various embodiments of the present invention for illustrative purposes and are not intended to limit the claims in any way. Indeed, various modifications of the invention are likely possible with continued experimentation by skilled practitioners of the art. Such modifications are intended to fall within the scope of the invention.

EXAMPLES

General Procedure

The compositions used in the following examples were prepared in quantities ranging from 25 grams to 150 pounds by first preparing a pH-adjusted admixture using either of the two pH-adjusting methods discussed above in the "Detailed Description of the Invention." The term "admixture" as used herein refers to an intimate mixture of the Fluthiamide and Metribuzin active ingredient materials (hereinafter referred to as "a.i.") in combination with one or more additional ingredients, known as inert ingredients or formulation aids, such that the admixed composition has the necessary performance properties to function by itself as a dry herbicidal composition when applied by any of the customary application techniques.

To facilitate intimate mixing of the admixture components, the individual ingredients were first blended in a mixing vessel, such as a ribbon blender, or high-intensity plow mixer, or, if the sample was small, the materials were agitated together manually in a polyethylene bag. This coarse blending was then followed by a particle size reduction procedure using either a hammermill or an air mill (e.g. ring type), or combination of hammermill plus airmill, in order to achieve the desired average particle size range of approximately 5 to 10 microns, in addition to providing additional blending of the admixture. At this point, the admixture was a dry powder having the composition and characteristics of a water-dispersible powder ("wettable powder" or WP). The admixture can be used commercially as such, or, the admixture can be further granulated into a water-dispersible granule (WDG). When the admixture is further granulated into a WDG, the admixture is referred to as a granulation "premix".

In the following examples, the compositions were tested in either the WP (i.e., premix) or WDG mode, and in one instance, in both modes. When prepared as a WDG, the premix was granulated on a pan granulator, which is also referred to as a disk pelletizer. The granulating fluid was typically water, but could also contain additional solubilized formulation ingredients, such as wetting agents, emulsifiers, or the dispersants as described in the "Detailed Description of the Invention," or mixtures thereof, or additional pH-adjusting agents.

Following granulation, the wet WDG exits the granulating disk, whereupon it is collected and dried, preferably, in a fluid-bed dryer (e.g. Niro-Aeromatic, Inc.). Other drying methods, such as tray drying, vacuum drying, or oven drying may be used as long as the drying is accomplished promptly after the product exits the granulator and the maximum allowable product temperature is not exceeded. After drying, the WDG is sieved to a uniform granular size of approximately 10/40 Mesh. The pH-adjusted premix also lends itself to other agglomeration techniques, such as extrusion, Schugi processing, spray drying, spray agglomeration, or dry compaction, once the proper adjustments are made to fit the premix to the process. The recipes shown in the examples are expressed in weight percent (% w/w.). Active ingredient assays are shown either as absolute percent by weight (real-time storage studies) or as normalized percent, where the magnitude of the measurement is reported on a scale of 0% to 100%, with 100% being the reference point representing the maximum attainable value (accelerated stability tests).

Example 1

Demonstration of Chemical Instability of Fluthiamide and Metribuzin Formulation when Stored and Heated to 40° C. and 50° C.

A Fluthiamide and Metribuzin formulation having a 4:1 molar ratio of Fluthiamide to Metribuzin, was prepared as a WDG on a 16" diameter pan granulator using the general procedure outlined above. The sample was split and put into two polyethylene containers. One sample container was placed at a temperature of about 40° C. for 16 weeks, and the other at about 50° C. for 8 weeks. At the end of the 8 and 16 week storage periods, the WDG compositions were subjected to high performance liquid chromatography analysis (hereinafter referred to as "HPLC").

As shown in Table 1 below, following heating and storage, both samples experienced a decrease in Fluthiamide and Metribuzin compared to the initial. The analysis showed that the decrease in active ingredient was due to the hydrolysis of the Metribuzin and the hydrolysis and N-isomerization of the Fluthiamide. Table 1 also shows that the decrease in active ingredients was greater at 50° C. than at 40° C.

TABLE 1

Storage Stability (% A.I.) of Fluthiamide & Metribuzin Formulation Sample (93-100-54)

| Ingredient | Initial % | 40° C./16 Weeks | 50° C./8 Weeks |
|---|---|---|---|
| Fluthiamide | 54.9 | 50.5 | 49.2 |
| Metribuzin | 14.1 | 12.9 | 12.8 |

This example demonstrates the potential chemical decomposition that can occur to Fluthiamide/Metribuzin mixtures if the mixtures are subjected to heating at 40° C. and 50° C. for an extended period of time. Such conditions could be encountered in a storage facility where pesticidal products are likely to be stored.

Example 2

Stability Study of Fluthiamide and Metribuzin Formulations Using an Accelerated Stability Test It was found that the hydrolysis and N-isomerization of the active ingredients (as shown above in Table 1) could be quantitatively simulated by heating a mixture of the ingredients to a temperature of from about 100° C. to about 110° C. for a time period of about 16 hours (the "accelerated stability test").

About 50 grams of a Fluthiamide and Metribuzin admixture was charged to a 250 ml round bottom flask having a cold water condenser. The process was repeated with two additional samples. The flasks were labeled FDL 94-103-30, -32, and -33. None of the mixtures contained a pH adjusting agent, and the pH of the mixtures were from about 5.7 to about 7.0. The reaction mixtures were heated to about 110° C. for about 16 hours and then injected into a HPLC instrument. The results, shown in Table 2, demonstrate that the Fluthiamide isomerized significantly in each of the samples.

TABLE 2

Accelerated Stability Test of Fluthiamide and Metribuzin Admixtures

| | Sample ID | | |
|---|---|---|---|
| Ingredients | 30 | 32 | 33 |
| Fluthiamide Technical, 100%, a.i. | 54.4 | 54.4 | 54.4 |
| Metribuzin Technical, 100%, a.i. | 13.6 | 13.6 | 13.6 |
| Morwet D-425[1] | 7.2 | 7.2 | 7.2 |
| Reax 907[2] | 3.3 | 3.3 | 3.3 |
| Wessalon S[3] | 3.0 | 3.0 | 3.0 |
| Zeolex 7A[4] | 2.0 | 2.0 | 2.0 |
| Barden Clay[5] | 12.3 | 8.3 | 10.3 |
| Attaclay[6] | — | 4.0 | 2.0 |
| pH | 5.7 | 7.0 | 6.6 |
| Fluthiamide N-isomer before cook | 1% | 1% | 1% |
| Fluthiamide N-isomer after 110° C./16 hrs; normalized % | 52% | 42% | 63% |

[1]Morwet D-425 is a sodium naphthalene sulfonate condensate available from Witco Corporation, 3200 Brookfield Street, Houston, Texas.
[2]Reax 907 is a sodium lignosulfonate from Westvaco, Chemical Division, P.O. Box 70848, Charleston Heights, South Carolina.
[3]Wessalon S is a synthetic precipitated silicone dioxide from DeGussa Corp., 65 Challenger Road, Ridgefield Park, New Jersey.

TABLE 2-continued

Accelerated Stability Test of Fluthiamide and Metribuzin Admixtures

| | Sample ID | | |
|---|---|---|---|
| Ingredients | 30 | 32 | 33 |

[4]Zeolex 7A is a precipitated sodium aluminosilicate from J. M. Huber Corp.
[5]Barden Clay is a kaolin clay from Kentucky-Tennessee Clay Co., P.O. Box 1307, Langley, South Carolina.
[6]Attaclay is an attapulgite clay from Englehard.

Example 3

Accelerated Stability Test Related to Real-Time Storage

To correlate the results of the accelerated stability test with an Actual storage study, as well as to determine the optimum temperature for the accelerated test, another admixture was prepared as described in Example 2 and subjected to the previously described round flask procedure. This time, three separate flasks were prepared and maintained at temperatures of about 60° C., 80° C. and the standard 110° C., for 1 to 3 days. At the same time, a 5-week storage study was initiated in a polyethylene container at a temperature of 50° C. At various times during the course of these tests, samples from each flask were analyzed by HPLC. The results are shown graphically in FIG. 1. FIG. 1 shows that any of the accelerated test temperatures (60° C., 80° C. or 110° C.) will approximate in 1 to 3 days the change that normally takes 4 weeks to occur at 50° C. Of these temperatures, 110° C. is shown to be the most efficient, giving equivalent results in 16 to 24 hours. Thus, the accelerated 110° C. test is a rapid and reliable means of predicting chemical stability of Fluthiamide/Metribuzin mixtures over a specific range of elevated temperature storage.

Example 4

Stability Study of a Composition Containing Fluthiamide, Acid-Treated Metribuzin, and a pH Adjusting Agent Compositions containing Fluthiamide and phosphoric acid-treated Metribuzin were prepared and examined for stability at high temperatures.

4.1 Acidification of Metribuzin

Four different phosphoric acid solutions (A–D) were prepared. Solution A contained 0.25 grams of phosphoric acid and 450 milliliters of distilled water. Solution B contained 0.50 grams of phosphoric acid and 450 milliliters of distilled water. Solution C contained 1.0 gram of phosphoric acid and 450 milliliters of distilled water. Solution D contained 5.0 grams of phosphoric acid and 450 milliliters of distilled water.

Ten (10) 25 gram samples of Metribuzin were prepared. These samples were labeled 92-34-146-1 to 92-34-146-8. In addition, two samples were labeled 92-34-146-5A and 92-34-146-5B. Each sample was placed into a funnel. About 200 milliliters of phosphoric acid from one of the phosphoric acid solutions described above (A–D) was poured over the Metribuzin as described in Table 3.1 below. The time it took for the solution to funnel through the Metribuzin sample was recorded as the solution time. After the phosphoric solution funneled through the Metribuzin sample, the samples were optionally washed with distilled water as shown in Table 3.1.

For those samples that were optionally rinsed with distilled water, the rinse was done approximately five (5) minutes after the acid solution was applied. After the rinse with the water, a vacuum was maintained for approximately fifteen (15) minutes. Each sample was then air dried under a hood or on a paper towel for approximately two and one-half days.

TABLE 3.1

| Sample No. | Solution Time | Solution (200 mls) | Rinsed with Distilled |
|---|---|---|---|
| 92-34-146-1 | 36 seconds | A | Yes |
| 92-34-146-2 | 37 seconds | A | No |
| 92-34-146-3 | 36 seconds | B | Yes |
| 92-34-146-4 | 37 seconds | B | No |
| 92-34-146-5 | 38 seconds | C | Yes |
| 92-34-146-5A | 38 seconds | C | Yes |
| 92-34-146-5B | 38 seconds | C | Yes |
| 92-34-146-6 | 42 seconds | C | No |
| 92-34-146-7 | 40 seconds | D | Yes |
| 92-34-146-8 | 40 seconds | D | No |

4.2 Preparing Compositions Containing Acid Treated Metribuzin, Fluthiamide, and a pH Adjusting Agent For each sample, the following ingredients were weighed out in grams and charged to a reaction vessel:

| Ingredients | Weighed out in Grams | % w/w |
|---|---|---|
| Fluthiamide Technical | 522.0 | 68.1 |
| Morwet D-425* | 64.8 | 8.4 |
| Reax 907** | 29.7 | 3.9 |
| Wessalon S*** | 54.0 | 7.0 |
| Citric Acid**** | 14.4 | 1.8 |
| Barden Clay***** | 81.9 | 10.7 |
| | 766.8 g | 100% |

*Morwet D-425 is sodium naphthalene formaldehyde condensate and is available from Witco Corporation, 3200 Brookfield Street, Houston, Texas.
**Reax 907 is lignosulfonic acid, sodium salt and is available from Westvaco, Chemical Division, P.O. Box 70848, Charleston Heights, South Carolina.
***Wessalon S is synthetic amorphous silicon dioxide hydrate and is available from Degussa Corporation, 65 Challenger Road, Ridgefield Park, New Jersey.
****Citric Acid is available from Haarmann & Reimer Corp. Food Ingredients Division, 1127 Myrtle Street, P.O. Box 932, Elkhart, Indiana.
*****Barden clay is kaolin clay (hydrated aluminum silicate) and is available from Kentucky-Tennessee Company, P.O. Box 1307, Langley, South Carolina.

About 17.04 grams of this premix were charged to a flask. To this premix was added 2.96 grams of the acid treated samples of Metribuzin described in Table 3.1. Each sample contained the following ingredients:

| INGREDIENTS | 100% AI BASIS % w/w PREMIX | 94.5/93/5% AI % w/w PREMIX |
|---|---|---|
| Fluthiamide Technical* | 54.8 | 58.0 |
| Metribuzin Technical** | 13.8 | 14.8 |
| Morwet D-425 | 7.2 | 7.2 |
| Reax 907 | 3.3 | 3.3 |
| Wessalon S | 6.0 | 6.0 |
| Citric Acid | 1.6 | 1.6 |
| Barden Clay | 13.3 | 9.1 |
| | 100.0 | 100.0 |

*4-25-0070 % A.I. @ 94.5 (KC Tech, flake composite)
**VARIOUS 93.5 (ACID WASHED METRIBUZIN TECH.)

The pH of each of the samples was then tested:

| Sample ID | pH of 5% solution |
|---|---|
| 92-34-146-1 | 3.3 |
| 92-34-146-2 | 3.3 |
| 92-34-146-3 | 3.3 |
| 92-34-146-4 | 3.3 |
| 92-34-146-5 | 3.3 |
| 92-34-146-5A | 5.5 |
| 92-34-146-5B | 4.05 |
| 92-34-146-6 | 3.3 |
| 92-34-146-7 | 3.25 |
| 92-34-146-8 | 3.3 |

4.3 Stability of the Samples at 110° C.

Each of the above samples was subjected to an accelerated stability test. The accelerated stability test involved heating each sample to a temperature of 110° C. for a period of 24 hours. The samples were then subjected to HPLC. The results are shown below in Table 3.2.

TABLE 3.2

Accelerated Stability Test (110° C.) for Metribuzin/Fluthiamide Mixture - Dry Flowable

| Metribuzin Wash #[(1)] | Metribuzin % | Fluthiamide % | Fluthiamide N-isomer % | Thiadone % | Diketo of Metribuzin % |
|---|---|---|---|---|---|
| 92-34-146-01 | 24.9 | 73.0 | 1.23 | — | — |
| 110° C. | 23.0 | 68.0 | 2.46 | — | 1.15 |
| 92-34-146-02 | 25.4 | 72.4 | 1.32 | — | — |
| 110° C. | 23.7 | 72.0 | 2.17 | — | 0.95 |
| 92-34-146-03 | 24.9 | 73.1 | 1.25 | — | — |
| 110° C. | 23.1 | 70.5 | 2.39 | — | 0.87 |
| 92-34-146-04 | 25.1 | 72.8 | 1.25 | — | — |

TABLE 3.2-continued

Accelerated Stability Test (110° C.) for Metribuzin/Fluthiamide Mixture - Dry Flowable

| Metribuzin Wash #[1] | Metribuzin % | Fluthiamide % | Fluthiamide N-isomer % | Thiadone % | Diketo of Metribuzin % |
|---|---|---|---|---|---|
| 110° C. | 26.2 | 67.1 | 2.49 | — | 0.92 |
| 92-34-146-05 | 25.3 | 72.6 | 1.22 | — | — |
| 110° C. | 24.4 | 71.9 | 2.07 | — | 0.89 |
| 92-34-146-06 | 25.0 | 72.2 | 1.24 | — | — |
| 110° C. | 22.2 | 70.0 | 3.17 | 2.88 | 1.06 |
| 92-34-146-07 | 25.44 | 71.8 | 1.20 | — | — |
|  | 23.8 | 68.9 | 1.90 | 3.59 | 0.90 |
| 92-34-146-08 | 25.1 | 72.2 | 1.20 | — | — |
|  | 23.7 | 66.0 | 2.10 | 4.54 | 0.91 |
| 92-34-146-05A | 29.1 | 68.7 | 1.27 | — | — |
|  | 25.9 | 35.4 | 35.2 | 2.33 | — |
| 92-34-146-5B | 26.5 | 70.9 | 1.21 | — | — |
|  | 25.1 | 62.6 | 5.04 | 4.32 | 0.38 |

[1]All the samples were premix.

The results in Table 3.2 demonstrate that the compositions prepared according to this example using the acid treated Metribuzin exhibit improved stability against hydrolysis and N-isomerization when compared with the compositions examined in Examples 1 and 2.

Example 5

Effect of Various Levels of Citric Acid on pH and Chemical Stability of Fluthiamide and Metribuzin Mixtures A series of granulation premixes were prepared by blending the individual ingredients together in a poly bag, followed by double hammermilling to reduce the particle size. In this series, citric acid was used as the pH adjusting agent. Each sample was placed in a 250-mL round bottom flask and subjected to the accelerated stability test, then analyzed by HPLC. The results are shown below in Table 4.

TABLE 4

Effect of Citric Acid on the Chemical Stability of Fluthiamide and Metribuzin Mixtures

| Ingredients | Sample ID | | | | | |
|---|---|---|---|---|---|---|
|  | 23 | 24 | 25 | 30 | 35A | 35B |
| Fluthiamide Tech, 100% ai | 54.5 | 54.5 | 54.5 | 54.5 | 54.5 | 54.5 |
| Metribuzin Tech, 100% ai | 13.6 | 13.6 | 13.6 | 13.6 | 13.6 | 13.6 |
| Morwet D425 | 7.2 | 8.0 | 7.2 | 7.2 | 7.2 | 0.0 |
| Reax 907 | 3.3 | 4.0 | 3.3 | 3.3 | 3.3 | 7.0 |
| Wessalon S | 3.0 | 6.1 | 2.0 | 3.0 | 17.2 | 20.6 |
| Zeolex 7A | 2.0 | 5.0 | 2.0 | 2.0 | 0.1 | 0.0 |
| Citric Acid | 4.5 | 4.5 | 7.0 | 0.0 | 0.1 | 0.1 |
| Barden Clay | 7.6 | 0.0 | 7.2 | 12.3 | 17.2 | 0.0 |
| pH | 3.0 | 3.1 | 2.8 | 5.7 | 5.4 | 5.5 |

TABLE 4-continued

Effect of Citric Acid on the Chemical Stability of Fluthiamide and Metribuzin Mixtures

| Ingredients | Sample ID | | | | | |
|---|---|---|---|---|---|---|
|  | 23 | 24 | 25 | 30 | 35A | 35B |
| Fluthiamide N-isomer before cook | nd | nd | 0.5% | 1% | 1% | 1% |
| Fluthiamide N-isomer after 100° C./16 hrs; normalized % | 0.8 | nd | 1 | 52 | 18 | 17 | nd = none detected

Example 6

The Effect of pH-Adjusting Agents on the Chemical Stability of Fluthiamide and Metribuzin Mixtures A series of admixtures, 25 grams each, similar to those described in the preceding examples were prepared by bag-blending the ingredients followed by double hammermilling. Additional pH-controlling ingredients were tested with Fluthiamide and Metribuzin admixtures. The common characteristic of these salts of organic and inorganic acids is that they all have an acid pH when solubilized, in the range of 4 to 5. The admixtures were placed in a 250-mL round-bottom flask and subjected to the accelerated stability test, followed by HPLC analysis. The results, presented in Table 5 below, demonstrate that significant suppression of Fluthiamide isomerization was achieved with ammonium sulfate, ammonium dihydrogen phosphate, and potassium dihydrogen phosphate.

TABLE 5

Effect of Various pH-Adjusting Agents on the Chemical Stability of Fluthiamide/Metribuzin

| | Sample ID | | | | | | |
|---|---|---|---|---|---|---|---|
| | 94-103- | 95-100-10 | | | | | |
| Ingredients | 36C | A1 | A2 | B | C | D | E |
| Fluthiamide Tech, 93% ai | 59.0 | 59.0 | 59.0 | 59.0 | 59.0 | 59.0 | 59.0 |
| Metribuzin Tech, 93% ai | 15.0 | 15.0 | 15.0 | 15.0 | 15.0 | 15.0 | 15.0 |
| Tamol SN[1] | 0.0 | 6.0 | 6.0 | 6.0 | 6.0 | 6.0 | 6.0 |
| Reax 907 | 0.0 | 4.0 | 4.0 | 4.0 | 4.0 | 4.0 | 4.0 |
| Wessalon S | 10.7 | 5.0 | 5.0 | 5.0 | 5.0 | 5.0 | 5.0 |
| Zeolex 7A | 0.0 | 0.0 | 0.0 | 0.0 | 0.0 | 0.0 | 0.0 |
| Citric Acid | 0.0 | 1.0 | 0.5 | 0.5 | 0.5 | 0.5 | 0.5 |
| Barden Clay | 0.0 | 3.0 | 3.0 | 3.5 | 3.5 | 3.5 | 3.5 |
| Baykanol SK | 8.0 | | | | | | |
| Ammonium Sulfate | 9.0 | | | | | | |
| Ammonium Chloride | | 7.0 | 7.0 | | | | |
| Ammonium $H_2$ Phosphate | | | | 7.0 | | | |
| Ammonium Citrate dibasic | | | | | 7.0 | | |
| Disodium Citrate 1.5 $H_2O$ | | | | | | 7.0 | |
| Potassium $H_2$ Phosphate | | | | | | | 7.0 |
| pH | 4.8 | 3.5 | 3.9 | 4.1 | 5.0 | 5.0 | 4.1 |
| Fluthiamide N-isomer before cook | 1% | 1.5% | 1.5% | 1.5% | 1.5% | 1.5% | 1.5% |
| Fluthiamide N-isomer after 110° C. 16 hrs; normalized % | 4 | 52 | 56 | 5 | 27 | 48.5 | 5 |

[1]Tamol SN is a sodium naphthalene sulfonate formaldehyde condensate from Rohm & Haas Co.

Example 7

The Effect of Various Levels of Ammonium Sulfate and Citric Acid on Stability of Fluthiamide and Metribuzin Admixtures A series of admixtures of Fluthiamide and Metribuzin were prepared in which different levels of ammonium sulfate and citric acid (the pH adjusted agents) were investigated in combination with the introduction of alternative surfactant materials. Each admixture was bag blended and milled through a Raymond Hammermill. The resulting powders, also known as granulation premixes, were tested as such for active ingredient (a.i.) stability by means of the accelerated stability test (heated to 110° C. for 16 hours) except for two samples which were pan granulated into dry flowable on a 10" disc (Samples 44 and 45 in Table 6 below). This was to facilitate the delivery of the liquid surfactants involved, namely Agrimul 2067 and DowFax C10-L, by incorporation into the granulating fluid (i.e., surfactant and water). These later two samples, after drying a fluid bed dryer using 60° C. air to a final moisture content of about 1% were then similarly tested for a.i. stability by the accelerated stability test. The results shown in Table 6 below demonstrate a significant a.i. stabilizing effect across a broad range of pH adjusting agent.

TABLE 6

Effect of Various Levels of Ammonium Sulfate on the Stability of Fluthiamide and Metribuzin

| | Sample ID | | | | | | | | | |
|---|---|---|---|---|---|---|---|---|---|---|
| | 94-103- | | | | 95-100-19 | | | | 95-100-21 | |
| Ingredients | 42 | 43 | 44 | 45 | A | B | C | D | A | B |
| Fluthiamide Tech, 93% ai | 59.0 | 59.0 | 59.0 | 59.0 | 59.0 | 59.0 | 59.0 | 59.0 | 59.0 | 59.0 |
| Metribuzin Tech, 93% ai | 15.0 | 15.0 | 15.0 | 15.0 | 15.0 | 15.0 | 15.0 | 15.0 | 15.0 | 15.0 |
| Morwet D-425 | 7.5 | 0.0 | 0.0 | 0.0 | 0.0 | 0.0 | 0.0 | 0.0 | 0.0 | 0.0 |
| Reax 907 | 3.5 | 3.5 | 3.5 | 3.5 | 3.0 | 3.0 | 3.0 | 3.0 | 3.0 | 3.0 |
| Wessalon S | 7.8 | 4.0 | 9.8 | 8.3 | 6.0 | 6.0 | 6.0 | 6.0 | 6.0 | 6.0 |
| Zeolex 7A | 2.0 | 2.0 | 2.0 | 2.0 | — | — | — | — | — | — |
| Citric Acid | 0.0 | 0.0 | 0.0 | 0.0 | 0.5 | 0.5 | 1.0 | 1.0 | 1.2 | 1.5 |
| Barden Clay | 0.0 | 7.3 | 0.0 | 0.0 | 4.5 | 5.5 | 6.0 | 7.0 | 7.8 | 8.5 |
| Baykanol SL | — | 4.0 | 0.0 | 4.0 | | | | | | |
| Ammonium Sulfate | 7.0 | 7.0 | 7.0 | 7.0 | 6.0 | 5.0 | 4.0 | 3.0 | 2.0 | 1.0 |
| Rhodacal DSB 85[1] | — | — | 3.0 | — | | | | | | |
| Agrimul 2067[2] | — | — | — | 3.0 | | | | | | |
| DowFax C10-L[3] | — | — | 2.5 | — | | | | | | |

TABLE 6-continued

Effect of Various Levels of Ammonium Sulfate on the Stability of Fluthiamide and Metribuzin

| | Sample ID | | | | | | | | | |
|---|---|---|---|---|---|---|---|---|---|---|
| | 94-103- | | | | 95-100-19 | | | | 95-100-21 | |
| Ingredients | 42 | 43 | 44 | 45 | A | B | C | D | A | B |
| Tamol SN | — | — | — | — | 6.0 | 6.0 | 6.0 | 6.0 | 6.0 | 6.0 |
| pH | 5.6 | 5.4 | 5.45 | 5.4 | 3.9 | 3.8 | 3.45 | 3.4 | 3.4 | 3.3 |
| Fluthiamide N-isomer before cook | 1% | 1% | 1% | 1% | 1% | 1% | 1% | 1% | 1% | 1% |
| Fluthiamide N-isomer after 110° C. 16 hrs normalized % | 10 | 6 | 7 | 14 | 2.4 | 3.9 | 0.6 | 0.4 | 0.8 | 0.6 |

[1]Rhodacal DSB-85 is an alkyl diphenyloxide disulfonate from Rhone-Poulenc
[2]Agrimul 2067 is an alkylpolyglucoside from Henkel Corp.
[3]Dowfax C10-L is an alkyl diphenyloxide disulfonate from the Dow Chemical Co.

Example 8

Stability of Compositions Containing Fluthiamide, HCl-Treated Metribuzin, and a pH Adjusting Agent In this embodiment, hydrochloric acid (HCl) rather than phosphoric acid ($H_3PO_4$) was used to acidify the Metribuzin prior to its use in admixtures with Fluthiamide. Two 100 gram samples of Metribuzin were treated with concentrated HCl by slurrying each sample in 400 milliliters of water and progressively titrating in the HCl while measuring the pH. The pH of the Metribuzin slurry, or dispersion, decreased as the millieguivalents of HCl added increased, as follows:

| | pH | meq HCl |
|---|---|---|
| Sample A | 8.8 | 0.0 |
| | 6.7 | 0.095 |
| | 5.7 | 0.206 |
| | 5.4 | 0.38 |
| Sample B | 9.5 | 0.0 |
| | 6.8 | 0.16 |
| | 5.7 | 0.29 |
| | 4.7 | 0.49 |

The slurries were then filtered through a Buchner-type suction filter. With the solids collected in the funnel, Sample A was further rinsed with dilute HCl. Similarly, Sample B solids were also treated with dilute HCl while in the funnel, but, in addition, received a final rinse with pure water. The resulting Metribuzin solids were then removed from the filter and air-dried in a laboratory hood. Once dry (moisture about 1%), the HCl-washed Metribuzin samples were admixed with supporting formulation ingredients to create a series of compositions containing ammonium sulfate and/or citric acid as the pH-adjusting agent. In one sample (see #17 in Table 8), where citric acid is the sole pH-adjusting agent, its level is lowered to near zero, to maintain the mildly acid environment favored by the Fluthiamide. For comparison with a similar admixture using standard (non-acid treated) Metribuzin, sample #35B is included from Example Number 5. The samples, 25 grams each, were then milled in a Tec-Mar micro mill to reduce the particle size and tested as powders, or granulation premixes, by the accelerated stability test (110° C./24 hours). The results of this series are given in Table 7 below.

TABLE 7

The Use of HCl-Treated Metribuzin in Fluthiamide/Metribuzin Admixtures

| | Sample ID | | | | | |
|---|---|---|---|---|---|---|
| | Control | 95-100- | | | | |
| Ingredients | 35B | 13 | 14 | 15 | 16 | 17 |
| Fluthiamide Tech, 100% ai | 54.4 | 54.4 | 54.4 | 54.4 | 54.4 | 54.4 |
| Metribuzin, untreated | 13.6 | — | — | — | — | — |
| Metribuzin A, 100% ai | 0.0 | 13.6 | 13.6 | — | — | 13.6 |
| Metribuzin B, 100% ai | 0.0 | — | — | 13.6 | 13.6 | — |
| Reax 907 | 7.0 | 3.0 | 3.0 | 3.0 | 3.0 | 3.0 |
| Wessalon S | 20.6 | 8.8 | 6.0 | 8.8 | 6.0 | 6.0 |
| Tamol SN | 0.0 | 7.0 | 6.0 | 7.0 | 6.0 | 6.0 |
| Citric Acid | 0.1 | 0.2 | 1.5 | 0.2 | 1.5 | 0.2 |
| Barden Clay | 0.0 | 0.0 | 9.5 | 0.0 | 9.5 | 10.8 |
| Ammonium Sulfate | 0.0 | 7.0 | 0.0 | 7.0 | 0.0 | 0.0 |
| pH | 5.5 | 4.6 | 3.2 | 4.5 | 3.25 | 4.6 |
| Fluthiamide N-isomer before cook | 1% | 1.5% | 1.5% | 1.5% | 1.5% | 1.5% |
| Increase in Fluthiamide N-isomer after 110° C., 16 hrs, % | 17 | 3 | 0.4 | 2.3 | 0.2 | 1.5 |

Example 9

Use of Various Surfactants in Stable Compositions Containing Fluthiamide, Phosphoric Acid-Treated Metribuzin, and a pH-Adjusting Agent In this embodiment, advantage is taken of the Metribuzin acid-washing process to add a secondary surfactant with the eventual outcome of the surfactant becoming part of the final Fluthiamide/Metribuzin admixture. The following procedure was performed with the intent that said procedure could be incorporated simultaneously in with, or immediately following, a production-scale Metribuzin acid-treatment process. The use of this procedure simplifies the addition of liquid surfactants which would otherwise be more cumbersome to apply in a conventional pan granulation process. Further, applying the surfactant directly the active ingredient provides for a most efficient use of the surfactant in that a relatively small quantity of surfactant is placed where it is likely to do the most good. To a beaker containing 300 mL of water were added 75 grams of previously phosphoric acid-treated Metribuzin. After a slurry is formed by stirring, 9 grams of the test surfactant were added and the mixture stirred for 15 minutes, then vacuum filtered. The solids in the filter are intentionally not over suctioned so that the solids can retain a copious liquid coating (containing surfactant).

In these examples, the filter cake was suctioned to a moisture level of approximately 15%, from which the theoretical surfactant loading in the filter cake can be calculated.

The wet, surfactant-treated, acid-washed Metribuzin in the filter was then removed and air dried in a laboratory hood. The result is a free-flowing powdered technical material intimately coated with surfactant. The "rewashed", surfactant-coated, acid-treated Metribuzin was then combined with formulation aids, Fluthiamide technical, and a pH-adjusting agent to form an admixture, which was then passed twice through a Raymond Hammermill to form a granulation premix. Conversion to a dry flowable was perfluid bed dryer. This process was repeated for 11 samples, formed on a 10" pelletizing dish, followed by drying in a one of which was a control utilizing unrewashed acid-treated Metribuzin (no surfactant coating). Since the focus of this experiment set was to screen alternative surfactant candidates in a known stable environment, a pH-adjusting agent, (citric acid) was used to provide a robust acid environment favorable to the active ingredient matrix. The finished dry flowable samples were tested under constant temperature storage of 8 weeks at 25° C. (assay reference point), 40° C. and 50° C. The results are shown below in Table 8.

TABLE 8

The Stability of Fluthiamide and Acid Treated Metribuzin Dry Flowables Containing Alternative Surfactants

| Ingredients | \multicolumn{11}{c}{Sample ID 95-100-} |
|---|---|---|---|---|---|---|---|---|---|---|---|
| | 51B | 51C | 51D | 51E | 51F | 51G | 51H | 51I | 51J | 51K | 51L |
| Fluthiamide Tech, 100% ai | 54.8 | 54.8 | 54.8 | 54.8 | 54.8 | 54.8 | 54.8 | 54.8 | 54.8 | 54.8 | 54.8 |
| Metribuzin, A-wash, 100% ai | 13.8 | 13.8 | 13.8 | 13.8 | 13.8 | 13.8 | 13.8 | 13.8 | 13.8 | 13.8 | 13.8 |
| Reax 907 | 3.3 | 3.3 | 3.3 | 3.3 | 3.3 | 3.3 | 3.3 | 3.3 | 3.3 | 3.3 | 3.3 |
| Moret D-425 | 7.2 | 7.2 | 7.2 | 7.2 | 7.2 | 7.2 | 7.2 | 7.2 | 7.2 | 7.2 | 7.2 |
| Wessalon S | 4.0 | 4.0 | 4.0 | 4.0 | 4.0 | 4.0 | 4.0 | 4.0 | 4.0 | 4.0 | 4.0 |
| Zeolex 7A | 2.0 | 2.0 | 2.0 | 2.0 | 2.0 | 2.0 | 2.0 | 2.0 | 2.0 | 2.0 | 2.0 |
| Citric Acid | 1.5 | 1.5 | 1.5 | 1.5 | 1.5 | 1.5 | 1.5 | 1.5 | 1.5 | 1.5 | 1.5 |
| Barden Clay | 12.8 | 12.8 | 12.8 | 12.8 | 12.8 | 12.8 | 12.8 | 12.8 | 12.8 | 12.8 | 12.8 |
| T-Det N-6[1] | 0.6 | | | | | | | | | | |
| T-Det N-9.5[2] | | 0.6 | | | | | | | | | |
| Soprophor 4D382[3] | | | 0.6 | | | | | | | | |
| Silwet 806[4] | | | | 0.6 | | | | | | | |
| Pluraflo L1060[5] | | | | | 0.6 | | | | | | |
| B F Goodrich K-752[6] | | | | | | 0.6 | | | | | |
| Soprophor FLK[7] | | | | | | | 0.6 | | | | |
| Ethomeen S/15[8] | | | | | | | | 0.6 | | | |
| Gafac RE-610[9] | | | | | | | | | 0.6 | | |
| Tergitol 15-S-3[10] | | | | | | | | | | — | 0.6 |
| pH | 3.6 | 3.6 | 3.6 | 3.6 | 3.6 | 3.6 | 3.6 | 3.6 | 3.6 | 3.6 | 3.6 |
| 8 wks-25° C., % Fluthiamide/Metribuzin | 55.3/ 13.9 | 55.2/ 14.4 | 55.3/ 14.8 | 55.0/ 14.6 | 55.2/ 14.3 | 55.1/ 14.4 | 55.4/ 14.6 | 55.0/ 14.4 | 55.0/ 14.5 | 55.0/ 14.4 | 55.2/ 12.9 |
| 8 wks-25° C., % Fluthiamide/Metribuzin | 55.2/ 13.7 | 55.1/ 14.4 | 55.4/ 14.7 | 55.0/ 14.5 | 55.4/ 14.3 | 55.3/ 14.4 | 55.7/ 14.5 | 55.2/ 14.5 | 54.8/ 14.3 | 55.4/ 14.4 | 55.4/ 12.8 |
| 8 wks-25° C., % Fluthiamide/Metribuzin | 55.3/ 14.1 | 55.3/ 14.4 | 55.1/ 14.5 | 54.9/ 14.4 | 55.4/ 14.3 | 55.1/ 14.4 | 55.5/ 14.4 | 55.1/ 14.3 | 54.9/ 14.3 | 55.2/ 14.3 | 55.6/ 12.7 |

[1]T-Det N-6 is an ethoxylated alkylphenol from Harcros Chemicals, Inc.
[2]T-Det N-9.5 is an ethoxylated alkylphenol from Harcros Chemicals, Inc.
[3]Soprophor 4D384 is an ethoxylated trystyrylphenol from Rhone-Poulenc
[4]Silwet 806 is an silicone polyether copolymer from OSI Specialties, Inc.
[5]Pluraflo L1060 is an alkoxylated block copolymer from BASF
[6]K-752 is a sodium polyacrylate from B. F. Goodrich
[7]Soprophor FLK is an ethoxylated trystyrylphenol from Rhone-Poulenc
[8]Ethomeen/15 is an ethoxylated alkylamine from AKZO Nobel Chemicals, Inc.
[9]Rhodafac RE-610 is an ethoxylated phosphate ester from Rhone-Poulenc
[10]Tergitol 15-S-3 is an ethoxylated secondary alcohol from Union Carbide Example 10

Stable Formulation of Fluthiamide, Metribuzin and pH-Adjusting Agent in Wettable Powder and Dry Flowable Forms This example illustrates that when a pH-adjusting agent is added to a Fluthiamide and Metribuzin admixture, the resulting admixture is stable both in a powder form and granule form, thus allowing the same pH adjusting approach to be used for both agriculturally acceptable wettable powders or dry flowables containing Fluthiamide and Metribuzin. An admixture was prepared containing 54.5% Fluthiamide, 13.7% Metribuzin, 7.2% Morwet D425, 3.3% Reax 907, 4% Wessalon S (synthetic amorphous silica), 2% Zeolex 7A (sodium aluminosilicate), 1.5% citric acid and 10% kaolin clay. The combined ingredients were manually blended in a polyethylene bag, then hammermilled one pass in a Raymond Hammermill, followed by airmilling in a 4" airmill. The admixture at this point is technically considered a granulation premix, i.e., the powder that is about to undergo conversion to a granular form via pan granulation or other amenable granulation or dry compaction process. But, also at this point the premix has all the necessary formulation ingredients and properties to properly function as a commercial water-dispersible powder as well; and, therefore, can also be considered a Wettable Powder. In this example, a portion of the premix/wettable powder of Fluthiamide and Metribuzin was set aside for testing as a powder, and a portion was also pan-granulated into a dry flowable on a 16" disc to provide the equivalent water-dispersible granular form. Both forms were then subjected to the accelerated 110° C. stability test, the results of which are presented below in Table 9.

TABLE 9

The Chemical Stability of Fluthiamide and Metribuzin Containing a pH Adjusting Agent as Either Wettable Powder (Premix) or Dry Flowable (Assays Normalized to 100%)

| 95-100-35 | | Metribuzin % | Fluthi-amide % | N-isomer FOE % | Diketo Metrib % |
|---|---|---|---|---|---|
| PREMIX | Initial | 25.35 | 72.92 | | |
| | 100° C./ 24 h | 24.4 | 70.0 | 2.0 | |
| DRY FLOW-ABLE | Initial | 25.3 | 72.5 | | |
| | 100° C./ 24 h | 24.3 | 70.9 | 1.6 | 1.076 |

Example 11

Alternative Means of Applying pH-Adjusting Agent or Surfactants to Produce a Stable Fluthiamide and Metribuzin Dry Flowable Formulation In this example, the surfactants and/or the pH adjusting agent are charged to the formulation, in whole or in part, by means of the granulating fluid during pan granulation. This differs from the conventional method of adding the ingredients in their undiluted, usually dry state, to the dry premix during the preparation and granulating with water or similar binding fluid. In these examples demonstrating the alternative route, the selected additives were first dissolved in the granulating fluid (water) to a concentration of between 2% to 13%, then sprayed onto a previously prepared premix containing the Fluthiamide, Metribuzin and the formulating aids. The concentration of the selected additives in the spray are chosen based on the ingredient's role in the final formulation and its desired concentration in the final formulation. For example, a 6.2% citric acid solution sprayed to a level of 13.5% granular moisture content delivers approximately 1.0% citric acid to the final dried dry flowable formulation. After preparation on the 16" pan granulator and fluid bed dryer, the samples in these examples were placed under accelerated elevated temperature storage. The results are shown below in Table 10.

TABLE 10

The Stability of Fluthiamide and Metribuzin Dry Flowable Containing a Sprayed On pH-Adjusting Agent and Sprayed On Surfactant(s)

| Ingredient | FDL95-100-53 | FLD95-100-54 |
|---|---|---|
| Fluthiamide, 100% ai basis | 54.9 | 54.8 |
| Metribuzin, 100% ai basis | 13.6 | — |
| Metribuzin, $H_3PO_4$ washed, 100% ai | — | 13.7 |
| Morwet D-425 | 7.3 | 6.7 (4.3 dry + 2.4 wet) |
| Reax 907 | 3.3 | 3.3 |
| Wessalon S | 4.0 | 4.0 |
| Zeolex 7A | 2.1 | 2.0 |
| Citric Acid | 2.1 (1.2 dry + 0.9 wet) | 1.6 |
| T-Det N6[1] | 0.3 (wet) | — |
| Barden Clay | 8.3 | 9.9 |
| Granulating Fluid | 91.8% $H_2O$ 6.2% Citric acid 2.0 T-Det N6 | 84.0% $H_2O$ 13.0% Morwet D-425 |
| pH (Final Dry Flowable) | 3.1 | 3.38 |

| | FDL95-100-53 | | FDL95-100-54 | |
|---|---|---|---|---|
| Ingredient | Fluthi-amide % | Metrib. % | Fluthi-amide % | Metrib. % |
| Initial | 55.1 | 13.7 | 55.1 | 13.8 |
| 8 Weeks, Room Temp. | 54.4 | 13.7 | 54.9 | 13.7 |
| −25° C. | 53.1 | 13.3 | 55.0 | 13.8 |
| 40° C. | 54.5 | 13.6 | 55.2 | 13.8 |
| 50° C. | 54.0 | 12.9 | 54.4 | 13.4 |
| 16 Weeks, Room Temp. | 54.6 | 13.6 | 55.0 | 13.8 |
| −25° C. | 54.9 | 13.7 | 55.0 | 13.7 |
| 40° C. | 54.1 | 13.0 | 55.3 | 13.7 |
| 50° C. | — | — | — | — |
| 24 Weeks, Room Temp. | 53.7 | 13.6 | 55.1 | 14.0 |
| −25° C. | 53.6 | 13.6 | 51.9 | 12.5 |
| 40° C. | 53.9 | 13.6 | 55.0 | 13.7 |
| 50° C. | — | — | — | — |

[1]T-Det N-6 is an ethoxylated alkylphenol from Harcros, Inc.

Example 12

Stable Dry Flowable Formulation With Fluthiamide/Metribuzin Ratio Varied and Containing a pH Adjusting Agent In this example the molar ratio of Fluthiamide to Metribuzin is varied from about 4:1 to about 2:1. Varying the ratio allows the use of the formulation on other crops with specific dosage needs, and also demonstrates that the same pH adjusting principle is effective at more than one active ingredient ratio. In this example, a 60% total a.i. formulation was prepared by preparing a dry premix containing 40.1% Fluthiamide, 20.1% Metribuzin, 5.0% Morwet D425, 8.0% Reax 907, 4.0% Wessalon S, 2.0% Zeolex 7A, 1.5% Citric Acid, and 16.0% Barden Clay. This differs from previous examples in which a 68% total a.i. package was assembled (approximately 54.4% Fluthiamide, 13.6% Metribuzin). The dry premix was prepared using the general procedure of hammering once followed by airmilling in a 4" airmill. The premix was then granulated on a 16" pan granulator then dried in a fluid bed dryer. The final, dried Dry Flowable, which had a pH of 3.81, was then placed under accelerated elevated temperature storage as shown in Table 11.

TABLE 11

The Elevated Temperature Storage Stability of a Dry Flowable Containing a 2:1 Ratio of Fluthiamide to Metribuzin and a pH Adjusting Agent

| FDL95-100-42 | Fluthiamide % | Metribuzin % |
|---|---|---|
| Initial | 41.2 | 20.3 |
| 8 Weeks, Room Temp. | — | — |
| −25° C. | 41.5 | 20.3 |
| 40° C. | 40.9 | 20.0 |
| 50° C. | 39.0 | 19.8 |
| 16 Weeks, Room Temp. | 40.9 | 19.6 |
| −25° C. | 41.1 | 19.7 |
| 40° C. | 39.9 | 20.2 |
| 50° C. | — | — |
| 24 Weeks, Room Temp. | 40.8 | 20.0 |
| −25° C. | 41.0 | 20.0 |
| 40° C. | 38.6 | 19.7 |
| 50° C. | — | — |

Example 13

The Long Term Storage Stability of a Fluthiamide and Metribuzin Dry Flowable Containing pH Adjusting Agent In this example, a Fluthiamide and Metribuzin Dry Flowable formulation to which a pH adjustment had been applied by means of citric acid, is shown to have long term stability to at least one year. A micronized premix was first prepared by blending together 54.4% Fluthiamide, 13.6% Metribuzin, 3.3% Reax 907, 7.2% Morwet D-425, 4.0% Wessalon S, 2.0% Zeolex 7A, 1.3% Citric Acid and 15.2% Barden Clay in a high intensity plow mixer (Littleford Bros, Inc. Florence, Ky.) followed by airmilling in an 18" ring airmill. The premix was then afterblended to uniformity in a ribbon blender (Day Mixing Co, Cincinnati, Ohio), and then granulated with water on a 3½ foot diameter pan granulator and dried in a horizontal fluid bed dryer. The resulting Dry Flowable had a pH of 3.48. Representative samples were taken and placed under storage at four different temperature conditions, including one at ambient room temperature (RT) for one year. The results of the storage are shown below in Table 12.

TABLE 13

The Long Term Stability of Fluthiamide and Metribuzin Dry Flowable Containing a pH-Adjusting Agent

| 5-03-3011 | Fluthiamide % | Metribuzin % |
|---|---|---|
| Initial | 54.8 | 13.7 |
| 8 Weeks, Room Temp. | — | — |
| −25° C. | 55.8 | 13.8 |
| 40° C. | 54.8 | 13.5 |
| 50° C. | 54.1 | 13.3 |
| 16 Weeks, Room Temp. | — | — |
| −25° C. | 54.7 | 13.6 |
| 40° C. | 54.6 | 13.5 |
| 50° C. | — | — |
| 24 Weeks, Room Temp. | 54.7 | 13.4 |
| −25° C. | 54.5 | 13.4 |
| 40° C. | 54.0 | 13.3 |
| 50° C. | — | — |
| 1 year, Room Temp. | 55.0 | 13.5 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A stable dry herbicidal composition comprising:
   a) a N-(4-fluorophenyl)-N-(1-methylethyl)-2-[[5-(trifluoromethyl)-1,3,4-thiadiazol-2-yl]oxy]acetamide and 4-amino-6-(1,1-dimethylethyl)-3-(methylthio)-1,2,4-triazin-5(4H)-one mixture;
   b) from about 0.1% to about 10% by weight of a pH adjusting agent; and
   c) a pH of from about 2.8 to about 5.4,
   wherein the pH adjusting agent is selected from a group consisting of citric acid, and ammonium and potassium salts of sulfuric acid and phosphoric acid, and combinations thereof, and
   wherein the stable dry herbicidal composition excludes the presence of ammonium chloride, ammonium citrate, and disodium citrate.

2. The composition of claim 1 wherein the 4-amino-6-(1,1-dimethylethyl)-3-(methylthio)-1,2,4-triazin-5(4H)-one and N-(4-fluorophenyl)-N-(1-methylethyl)-2-[[5-(trifluoromethyl)-1,3,4-thiadiazol-2-yl]oxy]acetamide is present in a molar ratio from about 1:1 to about 1:6.

3. The composition of claim 1 wherein the 4-amino-6-(1,1-dimethylethyl)-3-(methylthio)-1,2,4-triazin-5(4H)-one and N-(4-fluorophenyl)-N-(1-methylethyl)-2-[[5-(trifluoromethyl)-1,3,4-thiadiazol-2-yl]oxy]acetamide is present in a molar ratio from about 1:1.2 to about 1:2.5.

4. The composition of claim 1 wherein 4-amino-6-(1,1-dimethylethyl)-3-(methylthio)-1,2,4-triazin-5(4H)-one has been treated with an acid.

5. The composition of claim 4 wherein the acid is selected from a group consisting of sulfuric acid, nitric acid, hydrochloric acid, phosphoric acid, a carboxylic acid and a dicarboxylic acid.

6. The composition of claim 1 wherein the pH adjusting agent is citric acid.

7. The composition of claim 1 wherein the pH adjusting agent is a mixture of citric acid and ammonium sulfate.

8. A method of preparing a stable dry flowable or dry composition comprising:
   a) combining N-(4-fluorophenyl)-N-(1-methylethyl)-2-[[5-(trifluoromethyl)-1,3,4-thiadiazol-2-yl]oxy]acetamide and 4-amino-6-(1,1-dimethylethyl)-3-(methylthio)-1,2,4-triazin-5(4H)-one to form a reaction mixture; and
   b) adding from about 0.1% to about 10% by weight of a pH adjusting agent, said composition having a pH of from about 2.8 to about 5.4, wherein the pH adjusting agent is selected from a group consisting of citric acid, and ammonium and potassium salts of sulfuric acid and phosphoric acid, and combinations thereof, and wherein the stable dry herbicidal composition excludes the presence of ammonium chloride, ammonium citrate, and disodium citrate.

9. The method of claim 8 wherein the 4-amino-6-(1,1-dimethylethyl)-3-(methylthio)-1,2,4-triazin-5(4H)-one and N-(4-fluorophenyl)-N-(1-methylethyl)-2-[[5-(trifluoromethyl)-1,3,4-thiadiazol-2-yl]oxy]acetamide is present in a molar ratio from about 1:1 to about 1:6.

10. The method of claim 8 wherein the 4-amino-6-(1,1-dimethylethyl)-3-(methylthio)-1,2,4-triazin-5(4H)-one and N-(4-fluorophenyl)-N-(1-methylethyl)-2-[[5-(trifluoromethyl)-1,3,4-thiadiazol-2-yl]oxy]acetamide is present in a molar ratio from about 1:12 to about 1:2.5.

11. The method of claim 8 further comprising the step of treating the 4-amino-6-(1,1-dimethylethyl)-3-(methylthio)-1,2,4-triazin-5(4H)-one with an acid prior to combining the N-(4-fluorophenyl)-N-(1-methylethyl)-2-[[5-trifluoromethyl)-1,3,4-thiadiazol-2-yl]oxy]acetamide with the 4-amino-6(1,1-dimethyl)-3-(methylthio)-1,2,4-triazin-5(4H)-one.

12. The method of claim 11 wherein the acid is selected from a group consisting of sulfuric acid, nitric acid, hydrochloric acid, phosphoric acid, a carboxylic acid or a dicarboxylic acid.

13. The method of claim 8 wherein the pH adjusting agent is citric acid.

14. The method of claim 8 wherein the pH adjusting agent is a mixture of citric acid and ammonium sulfate.

* * * * *